(12) United States Patent
Rohloff et al.

(10) Patent No.: US 7,959,938 B2
(45) Date of Patent: Jun. 14, 2011

(54) POLYOXAESTER SUSPENDING VEHICLES FOR USE WITH IMPLANTABLE DELIVERY SYSTEMS

(75) Inventors: Catherine Manya Rohloff, Los Altos, CA (US); Stephen Andrew Berry, Longview, WA (US); Ling-Ling Kang, Palo Alto, CA (US); Aruna Nathan, Bridgewater, NJ (US)

(73) Assignee: Intarcia Therapeutics, Inc., Hayward, CA (US)

( * ) Notice: Subject to any disclaimer, the term of this patent is extended or adjusted under 35 U.S.C. 154(b) by 870 days.

(21) Appl. No.: 11/374,228

(22) Filed: Mar. 13, 2006

(65) Prior Publication Data

US 2006/0246138 A1 Nov. 2, 2006

Related U.S. Application Data

(60) Provisional application No. 60/662,091, filed on Mar. 15, 2005.

(51) Int. Cl.
*A61F 13/00* (2006.01)
(52) U.S. Cl. ........................................................ 424/422
(58) Field of Classification Search .................... None
See application file for complete search history.

(56) References Cited

U.S. PATENT DOCUMENTS

| | | | |
|---|---|---|---|
| 3,987,790 A | 10/1976 | Eckenhoff et al. | 128/260 |
| 4,865,845 A | 9/1989 | Eckenhoff et al. | 424/424 |
| 4,892,778 A | 1/1990 | Theeuwes et al. | 428/218 |
| 4,915,949 A | 4/1990 | Wong et al. | 424/438 |
| 4,931,285 A | 6/1990 | Edgren et al. | 424/473 |
| 4,940,465 A | 7/1990 | Theeuwes et al. | 604/892.1 |
| 5,006,346 A | 4/1991 | Theeuwes et al. | 604/892.1 |
| 5,024,842 A | 6/1991 | Edgren et al. | 424/473 |
| 5,057,318 A | 10/1991 | Magruder et al. | 424/438 |
| 5,059,423 A | 10/1991 | Magruder et al. | 424/438 |
| 5,112,614 A | 5/1992 | Magruder et al. | 424/422 |
| 5,126,142 A | 6/1992 | Ayer et al. | 424/438 |
| 5,137,727 A | 8/1992 | Eckenhoff | 424/422 |
| 5,160,743 A | 11/1992 | Edgren et al. | 424/473 |
| 5,190,765 A | 3/1993 | Jao et al. | 424/473 |
| 5,234,692 A | 8/1993 | Magruder et al. | 424/473 |
| 5,234,693 A | 8/1993 | Magruder et al. | 424/473 |
| 5,252,338 A | 10/1993 | Jao et al. | 424/473 |
| 5,464,929 A * | 11/1995 | Bezwada et al. | 528/361 |
| 5,486,365 A | 1/1996 | Takado et al. | 424/602 |
| 5,595,751 A | 1/1997 | Bezwada | 424/422 |
| 5,597,579 A | 1/1997 | Bezwada et al. | 424/426 |
| 5,607,687 A | 3/1997 | Bezwada et al. | 424/426 |
| 5,618,552 A | 4/1997 | Bezwada et al. | 424/426 |
| 5,620,698 A | 4/1997 | Bezwada et al. | 424/426 |
| 5,620,705 A | 4/1997 | Dong et al. | 424/472 |
| 5,633,011 A | 5/1997 | Dong et al. | 424/451 |
| 5,645,850 A | 7/1997 | Bezwada et al. | 424/426 |
| 5,648,088 A | 7/1997 | Bezwada et al. | 424/426 |
| 5,660,861 A | 8/1997 | Jao et al. | 424/465 |
| 5,698,213 A | 12/1997 | Jamiolkowski et al. | 424/426 |
| 5,700,583 A | 12/1997 | Jamiolkowski et al. | 428/482 |
| 5,703,200 A | 12/1997 | Bezwada et al. | 528/354 |
| 5,728,396 A | 3/1998 | Peery et al. | 424/422 |
| 5,817,129 A | 10/1998 | Labrecque et al. | 606/228 |
| 5,844,017 A | 12/1998 | Jamiolkowski et al. | 522/33 |
| 5,859,150 A | 1/1999 | Jamiolkowski et al. | 525/437 |
| 5,904,935 A | 5/1999 | Eckenhoff et al. | |
| 5,932,547 A | 8/1999 | Stevenson et al. | 514/15 |
| 5,962,023 A | 10/1999 | Jamiolkowski et al. | 424/486 |
| 5,972,370 A | 10/1999 | Eckenhoff et al. | |
| 5,985,305 A | 11/1999 | Peery et al. | 424/422 |
| 5,997,527 A | 12/1999 | Gumucio et al. | |
| 6,074,660 A | 6/2000 | Jamiolkowski et al. | 424/426 |
| 6,100,346 A | 8/2000 | Jamiolkowski et al. | 525/419 |
| 6,113,938 A | 9/2000 | Chen et al. | 424/423 |
| 6,124,261 A | 9/2000 | Stevenson et al. | 514/12 |
| 6,132,420 A | 10/2000 | Dionne et al. | 604/892.1 |
| 6,147,168 A | 11/2000 | Jamiolkowski et al. | 525/437 |
| 6,156,331 A | 12/2000 | Peery et al. | 424/422 |
| 6,187,095 B1 | 2/2001 | Labrecque et al. | 118/110 |
| 6,224,894 B1 | 5/2001 | Jamiolkowski et al. | 424/426 |
| 6,235,712 B1 | 5/2001 | Stevenson et al. | |
| 6,251,435 B1 | 6/2001 | Jamiolkowski et al. | 424/486 |
| 6,270,787 B1 | 8/2001 | Ayer | |
| 6,287,295 B1 | 9/2001 | Chen et al. | |
| 6,372,256 B2 | 4/2002 | Jamiolkowski et al. | 424/486 |
| 6,375,978 B1 | 4/2002 | Kleiner et al. | |
| 6,395,292 B2 | 5/2002 | Peery et al. | 424/422 |
| 6,403,655 B1 | 6/2002 | Bezwada et al. | 514/772.7 |
| 6,458,385 B2 | 10/2002 | Jamiolkowski et al. | 424/486 |
| 6,508,808 B1 | 1/2003 | Eckenhoff et al. | |
| 6,514,517 B2 | 2/2003 | Jamilolkowski et al. | 424/426 |
| 6,524,305 B1 | 2/2003 | Peterson et al. | |
| 6,544,252 B1 | 4/2003 | Theeuwes et al. | |

(Continued)

FOREIGN PATENT DOCUMENTS

EP 0 841 359 A1 5/1998

*Primary Examiner* — Michael G Hartley
*Assistant Examiner* — Paul Dickinson
(74) *Attorney, Agent, or Firm* — Gary R. Fabian; Barbara G. McClung

(57) ABSTRACT

Liquid polyoxaester polymer materials are provided as suspending vehicles suitable for dispensing of pharmaceutically active agents, such as proteins, from delivery devices, for example, pump-driven dosage forms. Polyoxaesters are made from at least one diacid and at least one diol. Through the use of polyoxaesters virtually solvent-free pharmaceutical suspensions can be created.

18 Claims, 6 Drawing Sheets

U.S. PATENT DOCUMENTS

| | | |
|---|---|---|
| 6,939,556 B2 | 9/2005 | Lautenbach |
| 7,014,636 B2 | 3/2006 | Gilbert |
| 7,074,423 B2 | 7/2006 | Fereira et al. |
| 7,163,688 B2 | 1/2007 | Peery et al. |
| 7,207,982 B2 | 4/2007 | Dionne et al. |
| 7,258,869 B1 | 8/2007 | Berry et al. |
| 2001/0012511 A1 | 8/2001 | Bezwada et al. ............ 424/78.37 |
| 2001/0021377 A1 | 9/2001 | Jamiolkowski et al. ... 424/78.36 |
| 2001/0026793 A1 | 10/2001 | Jamiolkowski et al. ... 424/78.17 |
| 2002/0197185 A1 | 12/2002 | Jamiolkowski et al. ........... 42/29 |
| 2004/0224903 A1 | 11/2004 | Berry et al. |
| 2004/0243106 A1* | 12/2004 | Ayer .......................... 604/892.1 |
| 2005/0008661 A1 | 1/2005 | Fereira et al. |
| 2005/0112188 A1 | 5/2005 | Eliaz et al. |
| 2005/0175701 A1 | 8/2005 | Pan et al. |
| 2005/0266087 A1 | 12/2005 | Junnarkar et al. |
| 2005/0276856 A1 | 12/2005 | Fereira et al. |
| 2006/0193918 A1 | 8/2006 | Rohloff et al. |
| 2006/0216242 A1 | 9/2006 | Rohloff et al. |
| 2006/0246138 A1 | 11/2006 | Rohloff et al. |
| 2007/0027105 A1 | 2/2007 | Junnarkar et al. |
| 2007/0281024 A1 | 12/2007 | Lautenbach et al. |

* cited by examiner

POE I 3,6,9-trioxaundecanedioic acid starting monomer

POE II

Polyglycolic diacid starting monomer, n = 10-12

POLYOXAESTER SUSPENDING VEHICLES FOR USE WITH IMPLANTABLE DELIVERY SYSTEMS

CROSS-REFERENCE TO RELATED APPLICATIONS

This claims the benefit of priority under 35 U.S.C. §119(e) from provisional U.S. Application Ser. No. 60/662,091, filed on Mar. 15, 2005, which is incorporated herein by reference in its entirety.

FIELD OF THE INVENTION

The present invention relates to suspending vehicles and pharmaceutical suspensions in drug delivery systems and drug dosage forms utilizing the same.

BACKGROUND OF THE INVENTION

Ensuring stability of pharmaceutical agents within dosage forms that include suspensions is important, for example, for effective dosaging and/or shelf-stability. Pharmaceutical suspensions can be used, for example, in osmotic drug delivery devices and injection depot devices. Osmotically-driven, also referred to as pump-driven, devices include those described in U.S. Pat. Nos. 5,985,305; 6,113,938; 6,132,420, 6,156,331; 6,395,292, each of which is incorporated herein by reference.

One approach to providing a stable suspension of a pharmaceutical agent is to provide a dosage form containing a suspending vehicle whose viscosity is sufficiently high to slow the sedimentation rate of the pharmaceutical agent. Typically, suspending vehicles contain a high viscosity, biocompatible polymer and a water-immiscible solvent. Water-immiscible solvents are typically chosen for their tendency to limit water ingress into drug dosage forms that are exposed to aqueous media, for example, bodily fluids. Such solvents have been shown to provide stable environments for pharmaceutically active agents such as proteins and peptides.

Some biocompatible polymers, such as polyvinyl pyrolidone (PVP), exhibit some amount of solubility in water. As such, some suspending vehicles separate into two phases at an organic/aqueous interface at outlets of dosage forms. Under certain conditions, suspending vehicles comprising polymer in conjunction with a water-immiscible solvent may be difficult to pump through narrow exit ports of dosage forms. Further, reliability of dosage forms can be compromised by the formation of highly viscous, almost solid formations.

Hence, there exists a need to provide suspending vehicles made of a primary component that provides a stable environment for proteins and peptides that is substantially solvent-free. Also, there is a need to eliminate pluggage of discharge ports of implantable devices. Additionally, there is a need for suspending vehicles that use a primary component which exhibit desirable suspension characteristics while at the same time remain one-phase upon contact with aqueous media.

SUMMARY OF THE INVENTION

Generally, certain aspects of the invention provide pharmaceutical suspensions having polyoxaesters (POEs) as suspending vehicles. Polyoxaesters provide suitable characteristics for suspension and stability of pharmaceutically active agents, such as proteins, peptides, and small molecules, for use in conjunction with pump-driven dosages forms. Typically, vehicles and suspensions are substantially non-aqueous in order to maintain drug stability during storage and to limit ingress of water into the dosage forms.

In one aspect, the present invention provides pharmaceutical suspensions for use in pump-driven pharmaceutical dosage forms which comprise a pharmaceutically active agent and a polyoxaester. The polyoxaesters comprise reaction products of at least one diacid and at least one diol. In a detailed embodiment, the polyoxaesters have molecular weights from approximately 1,000 to approximately 100,000.

Preferable diacids for use with the present invention include, but are not limited to, polyglycolic diacids, 3, 6-trioxaundecanedioic diacids, 3, 6, 9-trioxaundecanedioic diacids, and combinations thereof.

Preferable diols for use with the present invention include, but are not limited to, ethyleneglycols, propanediols, butanediols, pentanediols, cyclopentanediol, hexanediols, cyclohexanediols, octanediols, decanediols, dodecanediols, cyclohexanedimethanol, polyethyleneglycol, polypropyleneglycol, and combinations thereof.

In a detailed embodiment of the invention, a dosage form is provided that comprises a first wall that maintains its physical and chemical integrity during the life of the dosage form and is substantially impermeable to a pharmaceutical suspension; a second wall that is partially permeable to an exterior fluid; a compartment defined by the first wall and the second wall; a pharmaceutical suspension that is positioned within the compartment and comprises a pharmaceutically active agent and a polyoxaester; a pump in communication with the first wall, the second wall, and the compartment; and an exit port in communication with the compartment. Preferably, the dosage form comprises an osmotic pump.

Also, in certain aspects, the pharmaceutical suspension is substantially flowable through the exit port of a dosage form under a force exerted by the pump under normal operating conditions.

Other examples of the present invention include pharmaceutical suspensions that are substantially homogeneous for at least 3 months at 37° C.

Methods include administering dosage forms containing pharmaceutical suspensions having polyoxaesters as suspending vehicles to a mammal. Kits include such dosage forms and instructions for their administration.

DETAILED DESCRIPTION OF ILLUSTRATIVE EMBODIMENTS

Liquid polyoxaester polymer materials are provided as suspending vehicles suitable for dispensing of pharmaceutically active agents, such as proteins, from delivery devices, for example, pump-driven dosage forms. Through the use of polyoxaesters (POEs), virtually solvent-free pharmaceutical suspensions can be created that exhibit virtually no phase separation at exit ports of pump-driven, for example, an osmotically-driven pump, dosage forms. Also, the formulation of one-component vehicles that are virtually solvent-free is simplified compared to multi-component formulations because only one component is needed.

Generally, polyoxaesters are biodegradable polymers that are formed by condensation reactions of oxadiacids and diols. Typically, polyoxaesters are one-phase, one-component liquid polymers that do not immediately harden or phase invert upon contact with aqueous media or during hydrolysis. Such polyoxaester polymers are also desirable due to the minimal aggregation of proteins therein. Polyoxaesters are absorbable by mammals, for example, they polymers hydrolyze into acids and alcohols within a few days. The POEs also do not accumulate in the body. Proteins are released relatively easily from a POE environment, relative to other polymer-based suspending vehicles which contain solvents, for example, benzyl alcohol with polyvinyl pyrrolidone. POEs tend to remain miscible with water or to stay soft when contacted with water. Also, POEs are desirable in the ability to control their viscosity at 35° C. based on reaction time.

Figure 1:
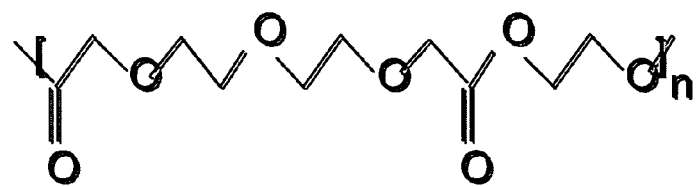
FIG. 1 shows a starting monomer for POEs: 3,6,9-trioxaundecanedioic acid.
Figure 2:
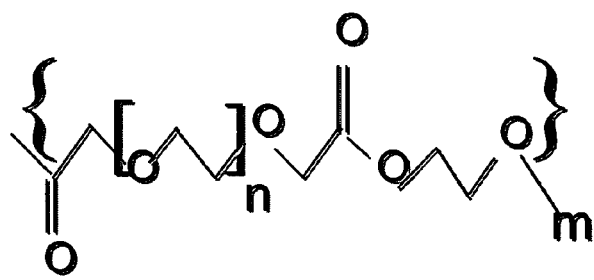
FIG. 2 shows a starting monomer for POEs: polyglycolic diacid.

With reference to FIG. 1, 3,6,9-trioxaundecanedioic acid is a preferable starting monomer for the POEs of the present invention. This monomer can be combined with at least one diol to create a POE polymer. "POE I" means a polymer derived from a mixture of 3,6,9-trioxaundecanedioic acid and ethyleneglycol as the starting monomers. With reference to FIG. 2, polyglycolic diacid is another preferable starting monomer for the POEs of the present invention. This monomer can be combined with at least one diol to create a POE polymer. "POE II" means a polymer derived from a mixture of polyglycolic diacid as a starting monomer.

Reference to "suspending vehicle" means that the pharmaceutically active agent is substantially insoluble therein. Materials that are substantially insoluble generally remain substantially in their original physical form throughout the lifespan of a dosage form containing the suspension. For example, solid particulates would generally remain particles. If necessary, the suspending vehicle may have other materials dissolved in it.

Although traditionally, in order to prevent particles in pharmaceutical suspensions from settling during the useful life of a dosage form, suspending vehicles having viscosities on the order of 10,000 poise at 35° C. were desirable. The settling rate of the particles is proportional to the density difference between the particle and the suspending medium. As such, lower viscosity-polymers can be used when they have densities that are substantially the same, or close, to typical protein particle densities, for example 1.2 g/mL. POE's of the present invention have densities that are close to densities of typical protein particles. As such, a lower viscosity may be sufficient to prevent particle settling during storage and use of a pharmaceutical implant.

Reference to "flowable" means that the suspending vehicles and pharmaceutical suspensions are able to flow out of a dosage form despite the possible presence of a second phase. As such, although some polymer-based gels may be present in the vehicles and suspensions upon contact with an aqueous medium, the vehicles and suspensions are substantially free of stiff gels, that is free of gels that are hard enough to impede flow out of the dosage form. Hence, although gels may be present, they are sufficiently pliable to permit the vehicle or suspension to flow out of the dosage form, for example, an osmotic dosage form. Preferably, suspending vehicles and pharmaceutical suspensions according to the present invention remain flowable upon contact with an aqueous medium under normal operating conditions of the dosage form.

Reference to "substantially free of solvents" means that the in pharmaceutical suspension that there is minimal use of solvents of the type that are typically used to thin highly viscous polymers for use suspending vehicles.

Polymers

Polymers useful in forming a vehicle according to the present invention include, but are not limited to, POE liquid polymers that result from condensation reactions of at least one diacid and at least one diol. Preferable diacids include, but are not limited to, polyglycolic diacid, 3,6-trioxaundecanedioic acid, 3,6,9-trioxaundecanedioic acid, and combinations thereof. Preferable diols include, but are not limited to, ethyleneglycols, propanediols, butanediols, pentanediols, cyclopentanediol, hexanediols, cyclohexanediols, octanediols, decanediols, dodecanediols, cyclohexanedimethanol, polyethyleneglycol, polypropyleneglycol, and combinations thereof. In some aspects of the invention, the molar ratio of the diacid to diol in the final polymer is approximately 1:1. Typically, during the reaction, the molar ratio of diacid to diol is <1. As such the molar ratio during the reaction is initially preferably approximately 1:2. Excess diol can be removed as needed, for example, by vacuum processing. In a detailed embodiment, the polyoxaesters have molecular weights ranging from approximately 1,000 to approximately 100,000.

Other examples of polymers useful in forming a pharmaceutical suspension or suspending vehicle according to the present invention include, but are not limited to, the polyoxaester polymers disclosed by U.S. Pat. Nos. 5,464,929; 5,607,687; 5,618,552; 5,620,698; 5,648,088; 5,859,150; 6,147,168; and 6,224,894 each of which is incorporated herein by reference. It may also be desirable to use polyoxaesters that contain amines and/or amido groups, for example, polyoxaamides, including, but not limited to polymers disclosed by U.S. Pat. Nos. 5,595,751; 5,597,579; 5,620,698; 5,645,850; 5,648,088; 5,844,017; 6,074,660; and 6,100,346.

Pharmaceutically Active Agents

"Pharmaceutically active agent" refers to any biologically or pharmacologically active substance or antigen-comprising material; the term includes drug substances which have utility in the treatment or prevention of diseases or disorders affecting animals or humans, or in the regulation of any animal or human physiological condition and it also includes any biologically active compound or composition which, when administered in an effective amount, has an effect on living cells or organisms.

Pharmaceutical suspensions can be created by mixing the pharmaceutically active agent with the suspending vehicle. In some embodiments, the pharmaceutically active agent included in a suspension according to the present invention is generally degradable in water but generally stable as a dry powder at ambient and physiological temperatures. Active agents that may be incorporated into a suspension according to the invention include, but are not limited to, peptides, proteins, nucleotides, polymers of amino acids or nucleic acid residues, hormones, viruses, antibodies, or small molecules etc. that are naturally derived, synthetically produced, or recombinantly produced. Preferably pharmaceutical suspensions remain substantially homogenous for about 3 months, even more preferably for about 6 months, and yet even more preferably, for about 1 year.

Preferably, the pharmaceutically active agent comprises lysozyme, interferon, erythropoietin, granulocyte macrophage colony stimulating factor (GM-CSF), human growth hormone releasing hormone (huGHRH), insulin, desmopressin, infliximab, an antibody, an agent conjugated to a targeting ligand, bone morphogenic proteins, Nesiritide, alpha-interferon, beta-interferon, omega-interferon, adrenocorticotropic hormone, angiotensin I, angiotensin II, atrial natriuretic peptide, bombesin, bradykinin, calcitonin, cerebellin, dynorphin N, alpha endorphin, beta endorphin, endothelin, enkephalin, epidermal growth factor, fertirelin, follicular gonadotropin releasing peptide, galanin, glucagon, glucagon-like peptide-1 (GLP-1), gonadorelin, gonadotropin, goserelin, growth hormone releasing peptide, histrelin, human growth hormone, insulin, leuprolide, LHRH, motilin, nafarerlin, neurotensin, oxytocin, relaxin, somatostatin, substance P, tumor necrosis factor, triptorelin, vasopressin, nerve growth factor, blood clotting factors, ribozymes, antisense oligonucleotide, or combinations thereof.

In other embodiments, the pharmaceutically active agent comprises risperidone, paliperidone, ocaperidone, or combinations thereof.

Other desirable active substances to all aspects of the invention can be the so-called antiherpes virus agents which have been or are developed for the treatment of herpes virus infections [herpes simplex virus types 1 and 2 (HSV-1 and HSV-2)], varicella zoster virus (VZV), cytomegalovirus (CMV), Epstein-Barr virus (EBV)]. The antiherpes virus agents include antiviral drugs and prodrugs thereof, such as nucleosides, nucleoside analogues, phosphorylated nucleosides (nucleotides), nucleotide analogues and salts, complexes and prodrugs thereof; e.g., guanosine analogues, deoxyguanosine analogues, guanine, guanine analogues, thymidine analogues, uracil analogues and adenine analogues. Antiherpes virus agent for use either alone or in combination in a composition according to the present invention can be selected from acyclovir, famciclovir, deciclovir, penciclovir, zidovudin, ganciclovir, didanosin, zalcitabin, valaciclovir, sorivudine, lobucavir, brivudine, cidofovir, n-docosanol, ISIS-2922, and salts, prodrugs, derivatives, analogues, and combinations thereof.

Other drugs which in themselves have a low water solubility, or the salts, esters, prodrugs or precursors of which have a low solubility may also be desirable in the compositions of the invention. Furthermore, it may be desirable to combine some active ingredients. As such, any of the foregoing examples can either alone or in combination can be incorporated in a composition according to the present invention. For example, a combination of active ingredients may include an anti-herpes virus agent and a glucocorticosteroid.

With respect to pharmaceutically active agents, pharmaceutical suspensions located in pump-driven dosage forms preferably comprise from about 0.5% to about 15% pharmaceutically active agent by weight, and possibly from about 0.1% to about 30%.

Pharmaceutical suspensions according to the present invention may include any pharmaceutically active agent that either exhibits desired solubility characteristics or may be prepared as a particulate material exhibiting desired solubility characteristics. Agents may be provided in the form of pharmaceutically acceptable salts, including salts with inorganic acids, organic acids, inorganic bases, organic bases, or combinations thereof. In some aspects, the agents are a biomolecular material, such as a peptide or protein that has biological activity or that may be used to treat a disease or other pathological condition. Analogs, derivatives, antagonists, and agonists of the exemplary peptides and proteins described may also be used. Agents are not limited to a biomolecular material. The drug may be any compound or material, including any medicine, vitamin, nutrient, or food supplement, which is capable of providing a therapeutic or beneficial affect when administered to an environment of operation and can be prepared as a particulate material exhibiting desired solubility characteristics.

The active agents included in a suspension according to the present invention may also include lipoproteins and post translationally modified forms, e.g., glycosylated proteins, as well as proteins or protein substances which have D-amino acids, modified, derivatized or non-naturally occurring amino acids in the D- or L-configuration and/or peptomimetic units as part of their structure. Specific examples of materials that may be included in as the pharmaceutically active agent in a suspension of the present invention include, but are not limited to, baclofen, GDNF, neurotrophic factors, conatonkin G, Ziconotide, clonidine, axokine, anitsense oligonucleotides, adrenocorticotropic hormone, angiotensin I and II, atrial natriuretic peptide, bombesin, bradykinin, calcitonin, cerebellin, dynorphin N, alpha and beta endorphin, endothelin, enkephalin, epidermal growth factor, fertirelin, follicular gonadotropin releasing peptide, galanin, glucagon, gonadorelin, gonadotropin, goserelin, growth hormone releasing peptide, histrelin, insulin, interferons, leuprolide, LHRH, motilin, nafarerlin, neurotensin, oxytocin, relaxin, somatostatin, substance P, tumor necrosis factor, triptorelin, vasopressin, growth hormone, nerve growth factor, blood clotting factors, ribozymes, and antisense oligonucleotides. Analogs, derivatives, antagonists agonists and pharmaceutically acceptable salts of each of the above mentioned active agents may also be used in formulating an active agent suspension of the present invention. Preferably, the active agents provided in a suspension of the present invention exhibits little or no solubility in the chosen suspension vehicle.

The active agents can be in various forms, such as uncharged molecules, molecular complexes, pharmacologically acceptable acid or base addition salts such as hydrochlorides, hydrobromides, sulfate, laurylate, palmitate, phosphate, nitrate, borate, acetate, maleate, tartrate, oleate, and salicylate. For acidic drugs, salts of metals, amines or organic cations, for example quaternary ammonium can be used. Derivatives of drugs such as esters, ethers and amides can be used alone or mixed with other drugs. Also, a drug that is water insoluble can be used in a form that on its release from a device, is converted by enzymes, hydrolyzed by body pH or other metabolic processes to the original form, or to a biologically active form.

With respect to pharmaceutically acceptable excipients and other processing aids, it is preferable that the drug particles incorporate any such excipients and/or aids into the solid drug particulate to be delivered from a suspension dosage form. As such, reference to drug particles or pharmaceutically active agents, includes any such excipients or aids incorporated therein.

Other desirable pharmaceutically active agents include, but are not limited to, the following groups: sodium fluoride, anti-inflammatory drugs such as, e.g., ibuprofen, indomethacin, naproxen, diclofenac, tolfenamic acid, piroxicam, and the like; narcotic antagonists such as, e.g., naloxone, nalorphine, and the like; antiparkinsonism agents such as, e.g., bromocriptine, biperidin, benzhexol, benztropine, and the like; antidepressants such as, e.g., imipramine, nortriptyline, pritiptylene, and the like; antibiotic agents such as, e.g., clindamycin, erythromycin, fusidic acid, gentamicin, mupirocien, amfomycin, neomycin, metronidazole, silver sulphadiazine, sulphamethizole, bacitracin, framycetin, polymycin B, acitromycin, and the like; antifungal agents such as, e.g., miconazol, ketoconazole, clotrimazole, amphotericin B, nystatin, mepyramin, econazol, fluconazol, flucytocine, griseoftdvin, bifonazole, amorolfine, mycostatin, itraconazole, terbenafine, terconazole, tolnaftate, and the like; antimicrobial agents such as, e.g., metronidazole, tetracyclines, oxytetracycline, and the like; antiemetics such as, e.g., metoclopramide, droperidol, haloperidol, promethazine, and the like; antihistamines such as, e.g., chlorpheniramine, terfenadine, triprolidine, and the like; antimigraine agents such as, e.g., dihydroergotamine, ergotamine, pizotyhne, and the like; coronary, cerebral or peripheral vasodilators such as, e.g., nifedipine, diltiazem, and the like; antianginals such as, e.g., glyceryl nitrate, isosorbide denitrate, molsidomine, verapamil, and the like; calcium channel blockers such as, e.g., verapamil, nifedipine, diltiazem, nicardipine, and the like; hormonal agents such as, e.g., estradiol, estron, estriol, polyestradiol, polyestriol, dienestrol, diethylstilbestrol, progesterone, dihydroergosterone, cyproterone, danazol, testosterone, and the like; contraceptive agents such as, e.g., ethynyl estradiol, lynestrenol, etynodiol, norethisterone, mestranol, norgestrel, levonorgestrel, desogestrel, medroxyprogesterone, and the like; antithrombotic agents such as, e.g., heparin, warfarin, and the like; diuretics such as, e.g., hydrochlorothiazide, flunarizine, minoxidil, and the like; antihypertensive agents such as, e.g., propanolol, metoprolol, clonidine, pindolol, and the like; corticosteroids such as, e.g., beclomethasone, betamethasone, betamethasone-17-valerate, betamethasone-dipropionate, clobetasol, clobetasol-17-butyrate, clobetasol-propionate, desonide, desoxymethasone, dexamethasone, diflucortolone, flumethasone, flumethasone-pivalate, fluocinolone acetonide, fluocinonide, hydrocortisone, hydrocortisone-17-butyrate, hydrocortisonebuteprate, methylprednisolone, triamcinolone acetonide, budesonide, halcinonide, fluprednide acetate, alklometasonedipropionate, fluocortolone, fluticason-propionate, mometasone-furate, desoxymethasone, diflurason-diacetate, halquinol, cliochinol, chlorchinaldol, fluocinolone-acetonid, and the like; dermatological agents such as, e.g., nitrofurantoin, dithranol, clioquinol, hydroxyquinoline, isotretionin, methoxsalen, methotrexate, tretionin, trioxsalen, salicylic acid, penicillamine, and the like; steroids such as, e.g., estradiol, progesterone, norethindrone, levonorgestrol, ethynodiol, levenorgestrel, norgestimate, gestanin, desogestrel, 3-keton-desogestrel, demegestone, promethoestrol, testosterone, spironolactone, and esters thereof, nitro compounds such as, e.g., amyl nitrates, nitroglycerine and isosorbide nitrates, opioid compounds such as, e.g., morphine and morphine-like drugs such as buprenorphine, oxymorphone, hydromorphone, levorphanol, fentanyl and fentanyl derivatives and analogues, prostaglandins such as, e.g., a member of the PGA, PGB, PGE, or PGF series such as, e.g., misoprostol, dinoproston, carboprost or enaprostil, a benzanide such as, e.g., metoclopramide, scopolamine, a peptide such as, e.g., growth hormone releasing factors, growth factors (epidermal growth factor (EGF), nerve growth factor (NGF), TGF, PDGF, insulin growth factor (IGF), fibroblast growth factor (FGFα, FGFβ, etc.), and the like), somatostatin, calcitonin, insulin, vasopressin, interferons, interleukins, e.g., IL-2, IL-12, IL-21, urokinase, serratiopeptidase, superoxide dismutase (SOD), thyrotropin releasing hormone (TRH), luteinizing hormone releasing hormone (LH-RH), corticotrophin releasing hormone (CRF), growth hormone releasing hormone (GHRH), oxytocin, erythropoietin (EPO), colony stimulating factor (CSF), and the like, a xanthine such as, e.g., caffeine, theophylline, a catecholamine such as, e.g., ephedrine, salbutamol, terbutaline, a dihydropyridine such as, e.g., nifedipine, a thiazide such as, e.g., hydrochlorotiazide, flunarizine, others such as, e.g., propanthelin, silver nitrate, enzymes like Streptokinases, Streptodases, vitamins like vitamin A, tretinoin, isotretionin, acitretin, vitamin D, calcipotriol, interferon-α-2b, selen disulfide, pyrethione.

It will be understood that the compositions of the invention can also comprise combinations of active substances, e.g., an active substance together with a potentiator therefor. It will of course also be understood that in the aspects of the invention wherein there is no specific requirement to the active substance, e.g., with respect to solubility, any substance which has a therapeutic or prophylactic activity can be incorporated in the composition.

Dosage Forms

Suspending vehicles and pharmaceutical suspensions can be prepared for use in all types of dosage forms, e.g., oral suspensions, ophthalmologic suspensions, implant suspensions, injection suspensions, and infusion suspensions. A preferred dosage form is an implantable osmotic dosage form such as those described in U.S. Pat. Nos. 5,985,305; 6,113,938; 6,132,420, 6,156,331; 6,395,292, each of which is incorporated herein by reference.

Typically, the implantable osmotic dosage form is a fluid-imbibing system that comprises an impermeable reservoir. The wall of the impermeable reservoir defines a first wall. The reservoir is divided into two chambers or compartments by a piston. The first chamber contains the pharmaceutically active agent and the second chamber contains a fluid-imbibing agent. A back-diffusion regulating outlet, comprising an exit port, is inserted into the open end of the first compartment and a water-swellable semi-permeable plug is inserted into the open end of the second chamber. The piston and the fluid-imbibing agent are components of an osmotic pump. The semi-permeable membrane defines a second wall. In general, the release rate of the active agent is governed by the osmotic pumping rate.

It is preferable that the polymers are physiologically acceptable for a desired route of administration, for example, there are no adverse biological responses by the recipient of the suspension upon administration. In some embodiments of the present invention, it is preferable that the components are suitable for parenteral routes of administration, including but not limited to injection, infusion, or implantation.

EXAMPLES

Below are several examples of specific embodiments for carrying out the present invention. The examples are offered for illustrative purposes only, and are not intended to limit the scope of the present invention in any way.

Example 1

Several POE liquid polymers were prepared and physical properties were analyzed as shown in Table 1. The polymers were prepared generally by mixing the desired molar ratios of the diacid(s) and diol(s) monomers and a catalyst in a 2 neck, round bottom flask, under a nitrogen purge and heating the mixture to ~160° C. slowly. The catalyst was dibutyltin oxide added at a ratio of 1 mole of catalyst to 30,000 mole monomer. Reactions typically started with a nominal molar ratio of approximately 1:2 diacid:diol, with the excess diol being removed under vacuum to result in a polymer that was approximately 1:1 diacid:diol.

The mixture was held at 160° C. for ~24 hours. The temperature was then raised to 180° C. and held there for ~24 hours. The mixture temperature was then reduced to 80° C. while vacuum was pulled slowly. Upon a vacuum of ~50 mTorr, the temperature was increased to 160° C. for 2-3 days.

Temperature was increased to 190° C. for a few hours until the sample became dark brown and viscous.

The methods disclosed by U.S. Pat. Nos. 5,464,929; 5,607,687; 5,618,552; 5,703,200; 5,859,150 6,147,168; 6,224,894; 6,403,655, each of which is incorporated herein by reference, can be used.

Onset of freezing was analyzed visually for the one sample, referred to as "POE I," which had a polymer composition of 1:1 molar of 3,6,9 trioxaundecanedioic acid and ethylene glycol.

Visual analysis of the onset of freezing was also used to evaluate the two samples referred to as "POE II," each of which had a polymer composition of 1:1 molar ratio of polyglycolic diacid and ethyleneglycol. As reaction time varies for polymers having approximately the same composition, the resulting molecular weights and viscosities will differ.

The other samples were analyzed using DSC, which is differential scanning calorimetry. Temperature is slowly increased (or decreased) and the changes in heat capacity of the sample material are monitored. In this way, DSC can measure phase transition temperatures.

The inherent viscosity of POE I was 0.37 dL/g as determined in HFIP at 25° C. and at a concentration of 0.1 g/dL. Average moisture of the POE I samples was 0.19% and the average peroxide level was 8.21 ppm.

Lysozyme particles were prepared by spray-drying an aqueous lysozyme solution. Lysozyme particles were collected and contained in lyophiliation vials in a low humidity environment. The POE I and the spray-dried lysozyme particles were weighed out according to a particle-loading of approximately 10% by weight of the pharmaceutical suspension, which corresponded to an active agent loading of approximately 10% by weight. The ingredients were mixed together with small spatula at room temperature in a dry box.

Release of protein from the suspension was determined in aqueous conditions and after undergoing an organic extraction. The POE I-based pharmaceutical suspension showed 91+/−1.3% released protein, based on ultraviolet (UV) absorbance, after 24 hours of incubation in a phosphate buffer solution at 37° C. The method for this in vitro protein release testing at 37° C. included dispensing approximately 10 mg of protein (lysozyme) pharmaceutical suspension in 3 mL of PBS buffer. The buffer/suspension mixture was incubated overnight at 37±1° C. incubator with constant shaking rate (Lindberg Blue water bath/shaker, speed set at 5). The process yielded a clear solution. The solution was filtered through a 0.2 μm membrane, diluted accordingly, and the protein content determined by UV and the purity by RP HPLC.

The percent of protein recovered by organic extraction was 90+/−1%, based on UV measurement. The method for protein extraction from the suspension using organic solvent included adding pre-chilled THF/acetone 50/50 (v/v) solvent mixture (e.g. 0.5 mL)) to the protein (lysozyme) pharmaceutical suspension (e.g. 10 mg). The solvent/suspension mixture was chilled on ice for a total of 30 min (with occasional mixing). The solvent/suspension mixture was spin-filtered

TABLE 1

| POE Polymers | | | | |
|---|---|---|---|---|
| Polymer Composition | | | | |
| Diacid:Diol Molar Ratio nominal starting ratio | Diacid Mol % | Diol Mol % | Onset of freezing | Viscosity at 35° C. (poise) |
| 1:2 | 100% polyglycolic diacid | 100% ethyleneglycol | Phase change between 5-15° C. | 1,000 |
| 1:2 | 100% polyglycolic diacid | 100% ethyleneglycol | Below 5° C., if any. | 100 |
| 1:2 | 100% 3, 6, 9 trioxaundecanedioic acid | 100% ethyleneglycol | Phase change between 5-25° C. | 3,500 |
| 1:2 | 100% polyglycolic diacid | 100% ethyleneglycol | 20° C. by DSC | 507 |
| 1:2 | 100% polyglycolic diacid | 100% ethyleneglycol | 20° C. by DSC | 707 |
| 1:2 | 100% polyglycolic diacid | 75% ethyleneglycol & 25% butanediol | 22° C. by DSC | 429 |
| 1:2 | 100% polyglycolic diacid | 100% hexanediol | 17° C. by DSC | 547 |
| 1:2 | 75% polyglycolic diacid & 25% 3, 6, 9 trioxaundecanedioic acid | 100% ethyleneglycol | 18° C. by DSC | 5,730 |
| 1:2 | 50% polyglycolic diacid & 50% 3, 6, 9 trioxaundecanedioic acid | 100% ethyleneglycol | No freezing. Tg ~−47° C. by DSC | 5,220 |

Example 2

POE I, a liquid polymer made from 3,6,9 trioxaundecanedioic acid and ethylene glycol, made in accordance with Example 1, was used as the suspending vehicle for a pharmaceutical suspension. The density of POE I was 1.29 g/mL+/−0.010. The method for measuring density of the suspension vehicle included taking an aliquot (e.g. 10 μL) of the suspension vehicle (POE), which was accurately weighed (using a balance with an accuracy of ±0.01 mg). The value for the density of the sample was derived from the resultant weight over the volume of the sample taken (g/mL). The measurement was repeated three times and the average value of the three measurements and the standard deviation reported.

through a 0.2 μm membrane to obtain a protein pellet. The retained protein pellet was air-dried, reconstituted in H₂O (e.g. 0.5 mL), mixed well, and allowed to sit at 2-8° C. for 1 hour. The clear protein solution was further diluted accordingly, and the protein content of the sample determined by UV, and the degree of protein degradation (purity) by reversed phase high performance chromatography (RP HPLC). The protein purity was determined to be 90% whether aqueous or organic environments were used to extract the lysozyme.

Example 3

Figure 3:
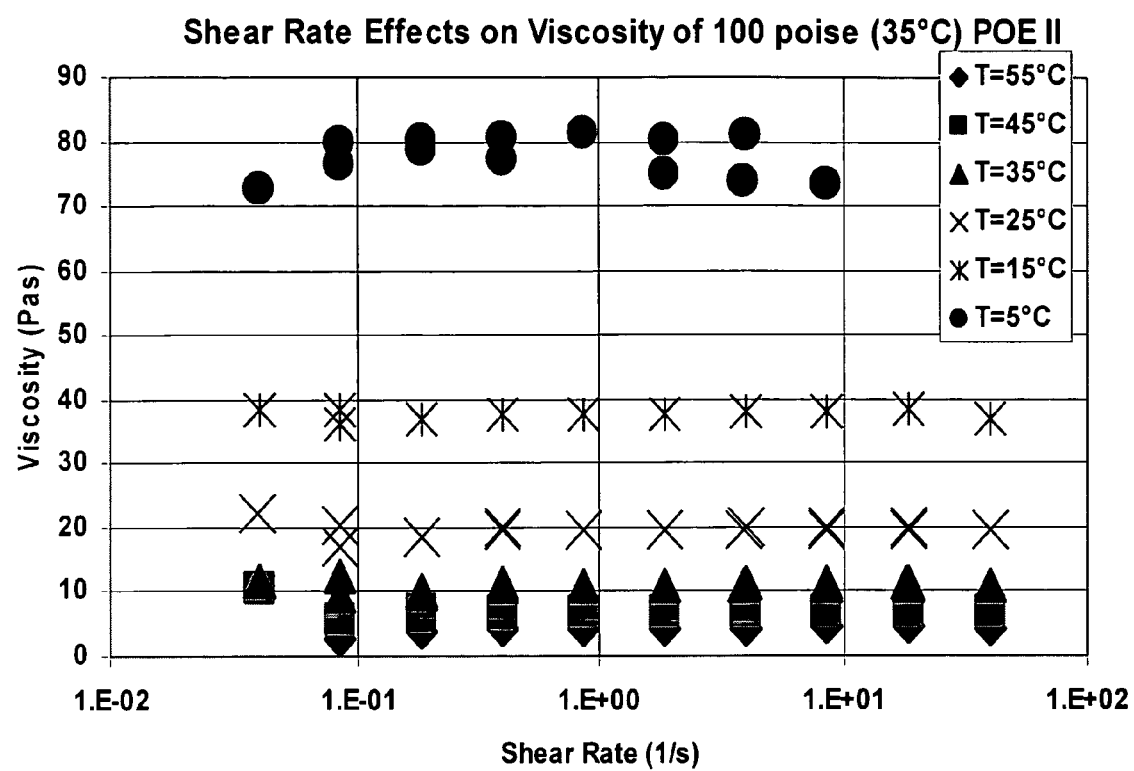
FIG. 3 shows viscosity versus shear rate for one batch of POE II, and the viscosity is 100 poise at 35° C.
Figure 4:
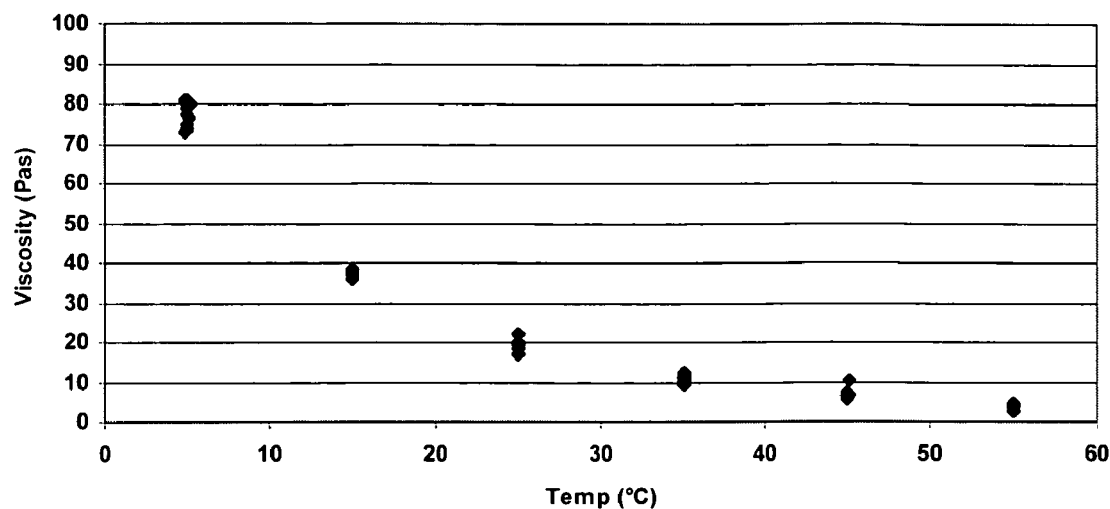
FIG. 4 shows viscosity versus temperature of for the same batch of POE II as shown in FIG. 3 (100 poise at 35° C.).

POE II, a liquid polymer made from polyglycolic diacid and ethylene glycol, having a viscosity of 100 poise (35° C.), made in accordance with Example 1, was used as the suspending vehicle for a pharmaceutical suspension. As shown in FIG. 3, there was no effect of shear rate on viscosity. FIG. 4 shows that no phase change occurred between 5° C. and 60° C., therefore, a phase change, if any, would occur at <5° C.

The density of the 100 poise (35° C.)-POE II was 1.18 g/mL+/−0.006. The method for measuring the density was as described in Example 2. The inherent viscosity of 100 poise POE II was 0.30 dL/g as determined in HFIP at 25° C. and at a concentration of 0.1 g/dL.

Average moisture of the 100 poise POE II samples was 0.11% and the average peroxide level was 6.44 ppm.

Lysozyme particles are prepared by spray-drying an aqueous lysozyme solution. Lysozyme particles are collected and contained in lyophiliation vials in a low humidity environment. The 100 poise (35° C.)-POE II and the spray-dried lysozyme particles were weighed out according to a particle-loading of approximately 10% by weight of the pharmaceutical suspension, which corresponded to an active agent loading of approximately 10% by weight. The ingredients were mixed together with small spatula at room temperature in a dry box.

Release of protein from the suspension was determined in aqueous conditions and after undergoing an organic extraction. The 100 poise (35° C.)-POE II-based pharmaceutical suspension showed 90+/−0.3% released protein, based on UV, after 24 hours of incubation in a phosphate buffer solution at 37° C. The method for protein release testing at 37° C. was as described in Example 2.

The percent of protein recovered by organic extraction was 97+/−2%, based on UV. The method for extraction of the protein was as described in Example 2.

Proteins are stable in the 100 poise (35° C.)-POE II-based pharmaceutical suspension as indicated by RP-HPLC measurements. These measurements indicate that the purity of the lysozyme is 90% and 95%, after aqueous and organic extraction, respectively.

Example 4

Figure 5:
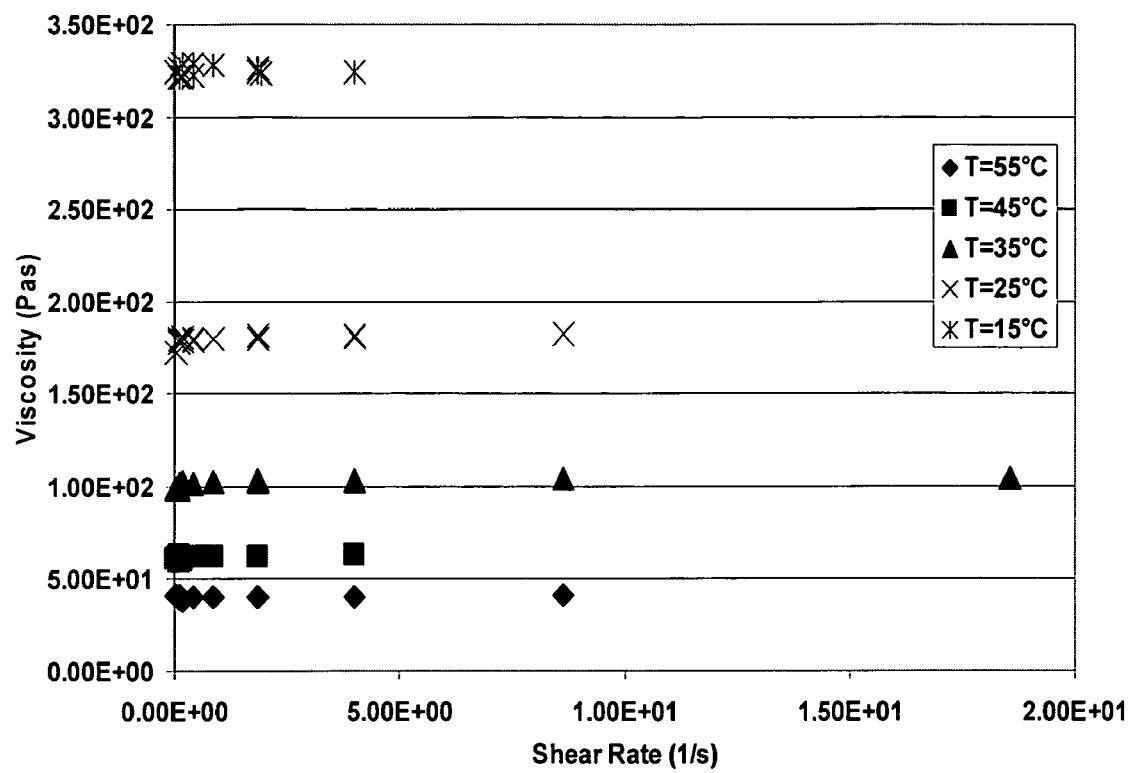
FIG. 5 shows viscosity versus shear rate for a second batch of POE II, and the viscosity is 1000 poise at 35° C.
Figure 6:
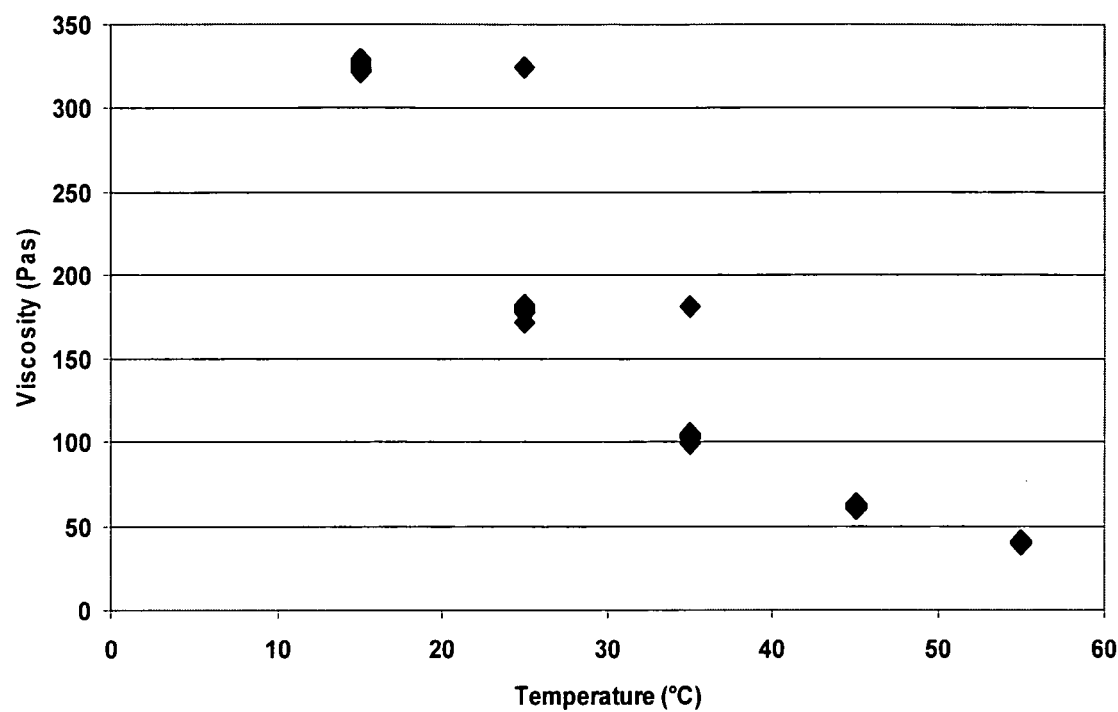
FIG. 6 shows viscosity versus temperature for the same batch of POE II as shown in FIG. 5 (1000 poise at 35° C.).

POE II, a liquid polymer made from polyglycolic diacid and ethylene glycol, having a viscosity of 1000 poise (35° C.), made in accordance with Example 1, was used as the suspending vehicle for a pharmaceutical suspension. As shown in FIG. 5, there was no effect of shear rate on viscosity. FIG. 6 shows the temperature effects on the viscosity of the polymer. Between 5° C. and 15° C., viscosity increased to unmeasurable values, and therefore, a phase change would occur at some point between 5° C. and 15° C.

The density of the 1000 poise (35° C.)-POE II was 1.18 g/mL+/−0.003. The method for measuring the density was as described in Example 2.

The inherent viscosity of 1000 poise POE II was 0.47 dL/g as determined in HFIP at 25° C. and at a concentration of 0.1 g/dL. Average moisture of the 1000 poise POE II samples was 0.07% and the average peroxide level was 3.79 ppm.

Lysozyme particles are prepared by spray-drying an aqueous lysozyme solution. Lysozyme particles are collected and contained in lyophiliation vials in a low humidity environment. The POE II and the spray-dried lysozyme particles were weighed out according to a particle-loading of approximately 10% by weight of the pharmaceutical suspension, which corresponded to an active agent loading of approximately 10% by weight. The ingredients were mixed together with small spatula at room temperature in a dry box.

Release of protein from the suspension was determined in aqueous conditions and after undergoing an organic extraction. The POE II-based pharmaceutical suspension showed 92+/−1.5% released protein, based on UV, after 24 hours of incubation in a phosphate buffer solution at 37° C. The method for protein release testing at 37° C. was as described in Example 2.

The percent of protein recovered by organic extraction was 93+/−1%, based on UV. The method for extraction of the protein was as described in Example 2. The HPLC measurements indicate that the purity of the lysozyme is 90% and 95%, after aqueous and organic extraction, respectively.

In vitro testing of a pharmaceutical suspension having a lysozyme loading of approximately 7% by weight in the 1000 poise (35° C.)-POE II was performed using DUROS implants. This suspension was loaded into 10 implantable, pump-driven dosage forms of the type disclosed in U.S. Pat. No. 6,395,292 for example. The release of the pharmaceutically active agent, for example, lysozyme, from the dosage form was determined analytically with UltraViolet spectrophotometry, and the integrity of the system as a whole was be observed visually.

First for each dosage form, a subassembly was prepared. A reservoir and a piston were lubricated. The piston was then inserted into the reservoir, followed by two osmotic tablets. Appropriate membranes were pressed into titanium reservoirs.

The pharmaceutical suspension was loaded into 5 ml SGE glass syringes to be de-aerated by mixing under heat and vacuum. Individual reservoir assemblies of the implantable devices were filled with the suspension.

The subassembly was heated to about 40° C. in a reservoir heater for at least 5 minutes, and then a diffusion moderator (DM) was put into the end of reservoir.

Ultraviolet-visible (UV) spectrometry was used to determine protein content delivered by the dosage forms. The method included the steps as described in Example 2.

Figure 7:
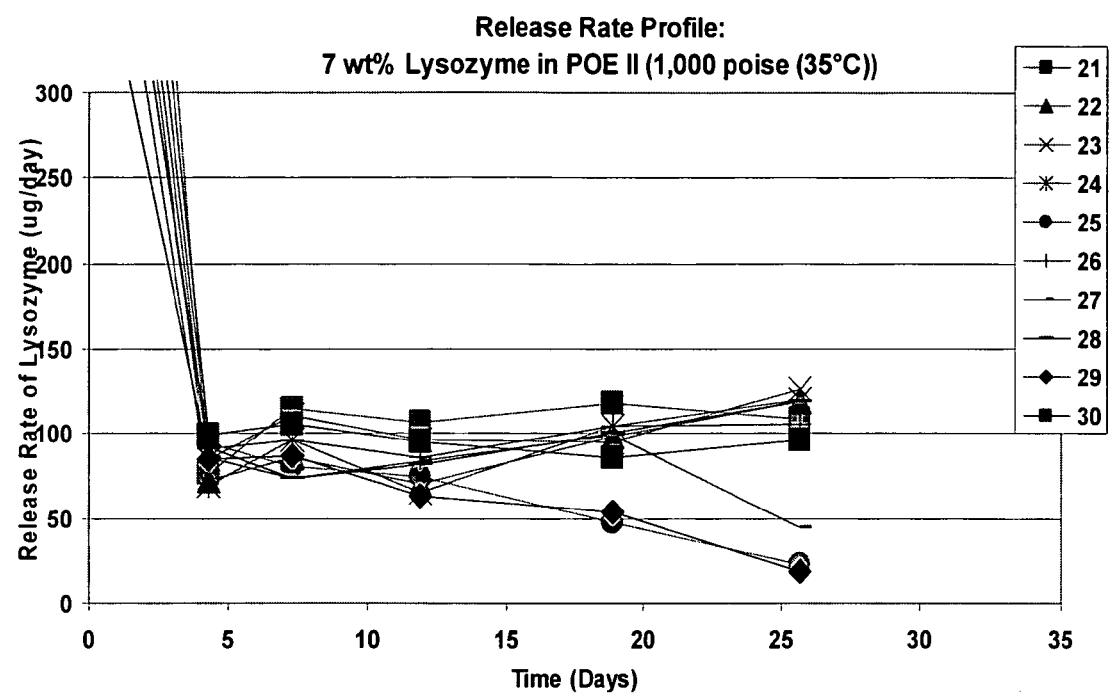
FIG. 7 shows a release rate profile of 7 wt % lysozyme in the 1000 poise (35° C.)-POE II.

As of day 33, 9 of the 10 dosage forms were delivering lysozyme. As shown in FIG. 7, a substantially zero-order delivery profile over a four week time period was achieved.

All publications, patents and patent applications cited herein are hereby incorporated by reference in their entirety. As used in this specification and the appended claims, the singular forms "a," "an" and "the" include plural references unless the content clearly dictates otherwise.

Other aspects of the invention will be apparent from review of the present specification and claims and all such falling within the spirit of the invention are comprehended hereby.

What is claimed:
1. An implantable osmotic dosage form comprising:
    a pharmaceutical suspension comprising (i) particles comprising a protein or peptide, and (ii) a suspending vehicle comprising a polyoxaester with an approximately 1:1 molar ratio of polyglycolic diacid and ethyleneglycol and having a density of about 1.2 g/mL, wherein the pharmaceutical suspension is substantially homogeneous for at least 3 months at 37° C.;
a first wall that maintains its physical and chemical integrity and is substantially impermeable to the pharmaceutical suspension;
a second wall that is partially permeable to an exterior fluid;
an osmotic pump in contact with the first wall and the second wall;
a compartment defined by the first wall and the osmotic pump, wherein the pharmaceutical suspension is positioned within the compartment; and
an exit port in communication with the compartment, wherein the pharmaceutical suspension is flowable through the exit port under a force exerted by the osmotic pump.

2. A method of making the dosage form of claim 1 comprising, loading the pharmaceutical suspension into the compartment.

3. The dosage form of claim 1, wherein the pharmaceutical suspension is substantially free of solvents.

4. The dosage form of claim 1, wherein the polyoxaester has a molecular weight of from approximately 1,000 to approximately 100,000.

5. The dosage form of claim 1, wherein the suspending vehicle consists essentially of the polyoxaester.

6. The dosage form of claim 1, wherein the osmotic pump comprises a piston and a fluid-imbibing agent.

7. An implantable osmotic dosage form comprising:
a pharmaceutical suspension comprising (i) particles comprising a protein or peptide, and (ii) a suspending vehicle comprising a polyoxaester with an approximately 1:1 molar ratio of polyglycolic diacid and ethyleneglycol and having a viscosity of about 100 poise at 35° C. and a density of 1.18 g/mL+/−0.006, wherein the pharmaceutical suspension is substantially homogeneous for at least 3 months at 37° C.;
a first wall that maintains its physical and chemical integrity and is substantially impermeable to the pharmaceutical suspension;
a second wall that is partially permeable to an exterior fluid;
an osmotic pump in contact with the first wall and the second wall;
a compartment defined by the first wall and the osmotic pump, wherein the pharmaceutical suspension is positioned within the compartment; and
an exit port in communication with the compartment, wherein the pharmaceutical suspension is flowable through the exit port under a force exerted by the osmotic pump.

8. A method of making the dosage form of claim 7 comprising, loading the pharmaceutical suspension into the compartment.

9. The dosage form of claim 7, wherein the pharmaceutical suspension is substantially free of solvents.

10. The dosage form of claim 7, wherein the polyoxaester has a molecular weight of from approximately 1,000 to approximately 100,000.

11. The dosage form of claim 7, wherein the suspending vehicle consists essentially of the polyoxaester.

12. The dosage form of claim 7, wherein the osmotic pump comprises a piston and a fluid-imbibing agent.

13. An implantable osmotic dosage form comprising:
a pharmaceutical suspension comprising (i) particles comprising a protein or peptide, and (ii) a suspending vehicle comprising a polyoxaester with an approximately 1:1 molar ratio of polyglycolic diacid and ethyleneglycol and having a viscosity of about 1000 poise at 35° C. and a density of 1.18 g/mL+/−0.003, wherein the pharmaceutical suspension is substantially homogeneous for at least 3 months at 37° C.;
a first wall that maintains its physical and chemical integrity and is substantially impermeable to the pharmaceutical suspension;
a second wall that is partially permeable to an exterior fluid;
an osmotic pump in contact with the first wall and the second wall;
a compartment defined by the first wall and the osmotic pump, wherein the pharmaceutical suspension is positioned within the compartment; and
an exit port in communication with the compartment, wherein the pharmaceutical suspension is flowable through the exit port under a force exerted by the osmotic pump.

14. A method of making the dosage form of claim 13 comprising, loading the pharmaceutical suspension into the compartment.

15. The dosage form of claim 13, wherein the pharmaceutical suspension is substantially free of solvents.

16. The dosage form of claim 13, wherein the polyoxaester has a molecular weight of from approximately 1,000 to approximately 100,000.

17. The dosage form of claim 13, wherein the suspending vehicle consists essentially of the polyoxaester.

18. The dosage form of claim 13, wherein the osmotic pump comprises a piston and a fluid-imbibing agent.

* * * * *